(12) United States Patent
Arikawa et al.

(10) Patent No.: US 12,286,662 B2
(45) Date of Patent: Apr. 29, 2025

(54) METHOD OF PRODUCING POLYHYDROXYALKANOATE

(71) Applicant: KANEKA CORPORATION, Osaka (JP)

(72) Inventors: Hisashi Arikawa, Takasago (JP); Shunsuke Sato, Takasago (JP); Yoshihiro Mouri, Takasago (JP)

(73) Assignee: KANEKA CORPORATION, Osaka (JP)

( * ) Notice: Subject to any disclaimer, the term of this patent is extended or adjusted under 35 U.S.C. 154(b) by 454 days.

(21) Appl. No.: 17/763,886

(22) PCT Filed: Aug. 5, 2020

(86) PCT No.: PCT/JP2020/029960
§ 371 (c)(1),
(2) Date: Mar. 25, 2022

(87) PCT Pub. No.: WO2021/059762
PCT Pub. Date: Apr. 1, 2021

(65) Prior Publication Data
US 2022/0411830 A1    Dec. 29, 2022

(30) Foreign Application Priority Data

Sep. 25, 2019 (JP) ................. 2019-173869

(51) Int. Cl.
*C12P 7/625*    (2022.01)
(52) U.S. Cl.
CPC .................................. *C12P 7/625* (2013.01)
(58) Field of Classification Search
None
See application file for complete search history.

(56) References Cited

U.S. PATENT DOCUMENTS

| | | | |
|---|---|---|---|
| 7,393,668 B2 * | 7/2008 | Yanagita ................ | C12P 7/625 435/135 |
| 10,519,473 B2 * | 12/2019 | Kobayashi ............ | C12Y 203/01 |
| 11,332,612 B2 * | 5/2022 | Nishiyama ............. | C08L 5/00 |
| 2011/0300592 A1 * | 12/2011 | Asai ....................... | C12P 7/625 435/135 |

FOREIGN PATENT DOCUMENTS

| | | |
|---|---|---|
| EP | 1 609 868 A1 | 12/2005 |
| WO | WO 2010/067541 A1 | 6/2010 |

OTHER PUBLICATIONS

International Search Report mailed on Oct. 6, 2020 in PCT/JP2020/029960 filed on Aug. 5, 2020 (3 pages).
Sedlacek, P. et al., "What keeps polyhydroxyalkanoates in bacterial cells amorphous? A derivation from stress exposure experiments", Applied Microbiology and Biotechnology, Jan. 8, 2019, vol. 103, pp. 1905-1917.
Anderson, A. J. et al., "Biosynthesis and composition of bacterial poly(hydroxyalkanoates)", Int. J. Biol. Macromol., Apr. 1990, vol. 12, total 4 pages.
Sato S et al., "Regulation of 3-hydroxyhexanoate composition in PHBH synthesized by recombinant *Cupriavidus necator* H16 from plant oil by using butyrate as a co-substrate", Journal of Bioscience and Bioengineering, 2015, vol. 120, No. 3, pp. 246-251.
Insomphun, C. et al., "Improved artificial pathway for biosynthesis of poly(3-hydroxybutyrate-co-3-hydroxyhexanoate) with high C6-monomer composition from fructose in *Ralstonia eutropha*", Metabolic Engineering, 2015, vol. 27, pp. 38-45.
Potter, M. et al., "Influence of homologous phasins (PhaP) on PHA accumulation and regulation of their expression by the transcriptional repressor PhaR in *Ralstonia eutropha* H16", Microbiology, 2005, vol. 151, pp. 825-833.

* cited by examiner

*Primary Examiner* — Christian L Fronda
(74) *Attorney, Agent, or Firm* — Oblon, McClelland, Maier & Neustadt, L.L.P.

(57) ABSTRACT

A polyhydroxyalkanoate-producing microorganism is cultured to obtain microbial bodies accumulating polyhydroxyalkanoate particles and having an average cell size of 2 μm or more. The microbial bodies are subjected to a heat treatment at a temperature higher than a temperature in the culturing to increase an average particle size of the polyhydroxyalkanoate particles in the microbial bodies. The resulting average particle size is equal to or greater than 1.8 μm and equal to or smaller than the average cell size. The microbial bodies subjected to the heat treatment can be disrupted to obtain a cell disruption solution. The PHA particles can be separated from an aqueous phase of the cell disruption solution.

19 Claims, 1 Drawing Sheet
Specification includes a Sequence Listing.

SEQUENCE LISTING

<160> NUMBER OF SEQ ID NOS: 4

<210> SEQ ID NO 1
<211> LENGTH: 926
<212> TYPE: DNA
<213> ORGANISM: Cupriavidus necator

<400> SEQUENCE: 1

```
agtgaattcg gatttaaata ccccctatacg cgcaagctga tggcggcggc gcaggtcggc    60
gctggctgac ccggaggtgt gcggcgcagc aacgccgcgg ccccgcctgg ctagcatccg   120
gttgttcgga tcaatccgat aaacaaggtg cgaattcccg cctatatcct tgattcgcca   180
gtcaaatccg gcgaatttgt aacgaacttt gacatgtgaa tgacaaccct ttaccatccc   240
gcgagaacta gttttggggg tggtccgtcc gacgcattgg atcgtgcata gcacgtttgc   300
ggtgcaagac aggcccggaa agcctggtgc ggatgttgca tagggttcac cccgcaggtt   360
cacatgaatt tctcgcgaag ttcacgcgaa tttcacatat aaccagctgc cccggacttg   420
tgccggggct tgctttggaa cgatcaacgg gagaaccagt ttccggcgcg ctacaagcaa   480
aaaggactgc tgcgacagtc cttttttctt tggcggggcg tgctccccgg gctattgcac   540
tgcgaccgtt ccgccggtg ccaggcgggc ctgttccagc cgctgccgca gcgttgccat   600
caccgccgtg gtggcctgtt cgccggccag tatggctcgg ttgcgggcgt tgaagtcgct   660
gccgcccata tcgggcagct cggggcggat caccacgtcg gcgcgcgcca gtgccatctt   720
gttgatcgac tggcccatga tcgcggtggt ctgcagcagc acgccgctct ggcccgcgtt   780
cttctgcgcc gacgggtcgg ccgagatgtt gaccgcgatg acaaagtccg cgcccatgcc   840
gcgcgcggaa tccaccggca ccggctcgac caggccgccg tcgacatagt cgtgaccctg   900
gatcgacatt taaatggata gctcgg                                        926
```

<210> SEQ ID NO 2
<211> LENGTH: 594
<212> TYPE: PRT
<213> ORGANISM: Aeromonas caviae

<400> SEQUENCE: 2

```
Met Ser Gln Pro Ser Tyr Gly Pro Leu Phe Glu Ala Leu Ala His Tyr
1               5                   10                  15
Asn Asp Lys Leu Leu Ala Met Ala Lys Ala Gln Thr Glu Arg Thr Ala
            20                  25                  30
```

-continued

```
Gln Ala Leu Gln Thr Asn Leu Asp Asp Leu Gly Gln Val Leu Glu
         35                  40                  45
Gln Gly Ser Gln Gln Pro Trp Gln Leu Ile Gln Ala Gln Met Asn Trp
 50                  55                  60
Trp Gln Asp Gln Leu Lys Leu Met Gln His Thr Leu Leu Lys Ser Ala
 65                  70                  75                  80
Gly Gln Pro Ser Glu Pro Val Ile Thr Pro Glu Arg Ser Asp Arg Arg
                 85                  90                  95
Phe Lys Ala Glu Ala Trp Ser Glu Gln Pro Ile Tyr Asp Tyr Leu Lys
                100                 105                 110
Gln Ser Tyr Leu Leu Thr Ala Arg His Leu Leu Ala Ser Val Asp Ala
            115                 120                 125
Leu Glu Gly Val Pro Gln Lys Ser Arg Glu Arg Leu Arg Phe Phe Thr
130                 135                 140
Arg Gln Tyr Val Ser Ala Met Ala Pro Ser Asn Phe Leu Ala Thr Asn
145                 150                 155                 160
Pro Glu Leu Leu Lys Leu Thr Leu Glu Ser Gly Gly Gln Asn Leu Val
                165                 170                 175
Arg Gly Leu Ala Leu Leu Ala Glu Asp Leu Glu Arg Ser Ala Asp Gln
            180                 185                 190
Leu Asn Ile Arg Leu Thr Asp Glu Ser Ala Phe Glu Leu Gly Arg Asp
        195                 200                 205
Leu Ala Leu Thr Pro Gly Arg Val Val Gln Arg Thr Glu Leu Tyr Glu
210                 215                 220
Leu Ile Gln Tyr Ser Pro Thr Thr Glu Thr Val Gly Lys Thr Pro Val
225                 230                 235                 240
Leu Ile Val Pro Pro Phe Ile Asn Lys Tyr Tyr Ile Met Asp Met Arg
                245                 250                 255
Pro Gln Asn Ser Leu Val Ala Trp Leu Val Ala Gln Gly Gln Thr Val
            260                 265                 270
Phe Met Ile Ser Trp Arg Asn Pro Gly Val Ala Gln Ala Gln Ile Asp
        275                 280                 285
Leu Asp Asp Tyr Val Val Asp Gly Val Ile Ala Ala Leu Asp Gly Val
290                 295                 300
Glu Ala Ala Thr Gly Glu Arg Glu Val His Gly Ile Gly Tyr Cys Ile
305                 310                 315                 320
Gly Gly Thr Ala Leu Ser Leu Ala Met Gly Trp Leu Ala Ala Arg Arg
                325                 330                 335
Gln Lys Gln Arg Val Arg Thr Ala Thr Leu Phe Thr Thr Leu Leu Asp
            340                 345                 350
Phe Ser Gln Pro Gly Glu Leu Gly Ile Phe Ile His Glu Pro Ile Ile
        355                 360                 365
Ala Ala Leu Glu Ala Gln Asn Glu Ala Lys Gly Ile Met Asp Gly Arg
370                 375                 380
Gln Leu Ala Val Ser Phe Ser Leu Leu Arg Glu Asn Ser Leu Tyr Trp
385                 390                 395                 400
Asn Tyr Tyr Ile Asp Ser Tyr Leu Lys Gly Gln Ser Pro Val Ala Phe
                405                 410                 415
Asp Leu Leu His Trp Asn Ser Asp Ser Thr Asn Val Ala Gly Lys Thr
            420                 425                 430
His Asn Ser Leu Leu Arg Arg Leu Tyr Leu Glu Asn Gln Leu Val Lys
        435                 440                 445
Gly Glu Leu Lys Ile Arg Asn Thr Arg Ile Asp Leu Gly Lys Val Lys
```

```
                450            455            460
Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
            485                 490                 495

Leu Leu Ala Glu Ser Gly His Ile Ala Gly Ile Ile Asn Pro Pro Ala
                500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
        530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 3
<211> LENGTH: 2478
<212> TYPE: DNA
<213> ORGANISM: Cupriavidus necator

<400> SEQUENCE: 3
agtgaattcg gatttaaatg ctaatggtga gtgtggtctt ggacatcgcg cctcctttac    60
tgcttgttgc cgctaatggc cgcgcaccta tgcagtgcat ccggcaggca ccagtctgaa   120
gccgctgcgc gcaacgcgcc gcgaagcggc gccatgccca tgcgccaggc gcatgcctcg   180
ctacttgcgc ggcattgtcc gcccgctcac agcacaatgc gcaaggcgcg tgccaggcat   240
aaactgatgg ccaattgtac gccgccccct gaccaggaac gccgggccag tcccggcgtt   300
tttttattct atagcgcaat taaccgccgt catattgcgt caccatgatt gccggatggc   360
cgcggcgatc ccttgctgga ggccggttcc aagaagattt aaagatgtca cggaattgtc   420
atacagggag catagagttc gtcttgtcaa aaatttgtca ttcccaacca atgttctctg   480
gaggacatat gtcccagaag aaatcgccac gcttcgagct gcgcagtggc aacgtagacg   540
ccctccttct cgccctccag accgccgaca tggctgcgct gcgggatgac ctcctcgccc   600
gctttgaagc cacccccgac ttcttttcca atgacgtgat tgcgctggac ctgcgcgcgc   660
tggaagatga cagcgaagtc gcgcttggca ccgtgatcga gacgctggcc acgctcaggg   720
cccgcgccat cggcgtggtg gcccgccccg gcagcgcga gtgggccgag cgcttcggcc   780
tgccgctgct ggacagccag gcccgccgcg gcagtggcgc cgatcgcgcc accgaccgtg   840
ccgccgaggc cagggccgca gccgcggcgg aacaggccgc agccgaccag gccgcgcgcg   900
aggaatccat ccgcgccgcc gcgcaggcca ccaccgacgc cgccgtggcc gctgccatcc   960
gccagaccca gaccatgctg atcgacaagc cgcttcgctc gggccagcag gtctacgcgc  1020
agggcgacgt ggtcatcctg gacgtggtca gctacgcgc cgaggtgatc gccgaaggca  1080
acatccatat ctatgccccg ctgcgcggcc gtgcgctggc gggcgtcaag ggcaacaccg  1140
gcgcgcgcat tttcagcacg tgcatggagc tgaactgat tccatcgcc ggcatctacc  1200
ggaccgcgga gcagacgctt ccggccgacg tgctcggcaa gaccgccag gtgcgcctgg  1260
ccgatgaaaa actgatcctg gaagcgctgc ggctcaagta accgcggcag ccccgggac  1320
```

```
cgaattgcag agagcgcaag cttcaactta ttactggacc aaagagccat ggcaaaaatc    1380
atcgttgtga cctccggcaa gggaggcgtc ggcaagacca ccaccagcgc cagctttgcc    1440
gccggcctgg ccctgcgcgg ccacaagact gccgtgatcg acttcgacgt cggcctgcgc    1500
aaccttgacc tgatcatggg ttgcgagcgc gcgtggtgt acgacctgat caacgtggtg     1560
cagggcgaag ccaacctgcg ccaggcgctg atcaaggaca agaagtgcga gaacctgttc    1620
atcctgccgg cctcgcagac gcgcgacaag gacgcgctca cgcgcgaagg cgtcgagaag    1680
gtcatcaacg gcctgatcga gatggatttc gaattcatca tctgcgactc gccggccggc    1740
atcgagtcgg gcgcgctgat ggcgatgtac ttcgccgacg aggcgctgat cgtgaccaac    1800
ccggaagtgt cgtcggtgcg cgattcggac cgcatcctgg gcatcctggc ctccaagacc    1860
aagcgcgcca cgaaggcgg cgacccgatc aaggaacacc tgctgatcac ccgctacaac    1920
cccaagcgtg tgcatggcgg cgaaatgctg tcgctgaccg acatccagga aatcctgcgc    1980
atcaagctga tcggcgtggt gccggagtct gaagccgtgc tgcacgcctc gaaccagggc    2040
acgcccgcca tccacctgga aggcagcgac gtggccgacg cctatggcga cgtggtggac    2100
cgcttcctcg gcaaggacaa gccgatgcgt ttcaccgact accagaagcc gggtctgctc    2160
tcccgcatct tcggcaacaa gtaacctgcc ggcctggttc aaccagtcgg cagccgacta    2220
gtcccggcag ccgccagcgc gctggcctcg cttatcatgg cagctgcgcc gggcggcacg    2280
cgaacggcgc ggcaccaacg atcaacatgc cattgctacc gacacaagac ttccagggcc    2340
agccgctggt ccggatcggc gatgccgaca cgttcctgct gctcgccccg caacacggcg    2400
ggcggctggt ccgctgggtg caccgcggac aggacatcct ctactggccg gacgctgcca    2460
tttaaatgga tagctcgg                                                  2478

<210> SEQ ID NO 4
<211> LENGTH: 956
<212> TYPE: DNA
<213> ORGANISM: Cupriavidus necator

<400> SEQUENCE: 4
agtgaattcg gatttaaatg tatgcggcat gtcactgggt tttgccgacc cggaagcgat     60
cgagaaccag ctgaccacgg aacgtgagcc ggtcagcggg ttcgcgcgtt tcctctcata    120
gcaaagtttg agaaaagttt gtatcaatgt gtaacgatga gtgccgatat acaagacgac    180
gtccgtgtat tggctgggag tgttccaagg ggcagcaagg tgaacccggg tacgcctggg    240
gcaagccaga ggcggttcgc atgcaaacgt gacctttgg ttgcttttc cgcaatgtgg      300 aaatgtttgc aaatcgaact ttaaggagcg tctgtaagtc tttaatcttg ctaacaattt    360 cttctttcc tacactagcg ccattcctat gcgctgaacg aatcatgttc cggtctgatt     420 ccatttttc cagattcttc ggctccgcac ccctgtccgc tgttgccacc gcggtcctgg     480
tatcgtacgg aacgcctgac cgggaaaaaa cgcgccgtgc cacggcgcgt ttttcgttct    540
ggcggccgcg gccgtcagag cagcttgcct gggttcatga tcccggccgg gtcgaacacg    600
gccttgatct cgcgcatcag ccgcagttcc agcgggtcct tcatggtcag gaaggcatgg    660
cgcttgagct ggccgatgcc atgctcggcg ctgatgctgc gccgtagcg catcacttcg     720 tccagcaccg cgtcggtcac cgcatcgcct tgcgtggccg cccagtcctt gggcgcgccg    780
```

-continued

```
gccgggcgcg acaggttgta gtgcaggttg ccgtcgccga agtgcccgaa gataaagggc      840
cggatggcgg gatcgagccc acgcagccgc gtttccatcg aggtcatgaa ggccggaatc      900
tgctcgatcg ggagcgagat gtcgtgcttc aggtgcgatt taaatggata gctcgg         956
```

METHOD OF PRODUCING POLYHYDROXYALKANOATE

TECHNICAL FIELD

The present invention relates to a method of producing a polyhydroxyalkanoate by culturing a polyhydroxyalkanoate-producing microorganism.

BACKGROUND ART

There is a growing awareness of environmental issues, food issues, health, and safety, and more and more people are becoming nature-oriented. Against such a background, material production using microorganisms (such as fermentative production and bioconversion) is becoming increasingly significant and important. Microbial material production is applied also to production of protein pharmaceuticals and production of nucleic acids for gene therapy. For example, ethanol production, acetic acid production, and medical protein production using microorganisms such as yeasts and bacteria are actively employed on an industrial scale.

An example of the microbial material production is microbial production of polyhydroxyalkanoates (also referred to as "PHAs" hereinafter) which are considered promising biodegradable plastics for industrial use (see Non Patent Literature 1). PHAs are thermoplastic polyesters produced and accumulated as energy storage materials in cells (also referred to as "microbial bodies" hereinafter) of many kinds of microorganisms and are biodegradable. Nowadays, the heightened environmental awareness has led to increasing attention to non-petroleum-based plastics. In particular, there is a strong demand for practical use of PHAs produced and accumulated in microbial bodies of microorganisms because such PHAs are absorbed into the carbon circulation process in the nature and are therefore expected to have little adverse impact on the ecosystems. A known example of PHA production using microorganisms is to produce a PHA by feeding bacteria of the genus *Cupriavidus* with a carbon source such as a sugar, vegetable oil, or fatty acid and thus allowing the bacteria to accumulate the PHA in their cells (see Non Patent Literatures 2 and 3).

However, microbial material production requires the complicated steps of separating and collecting the target product and could suffer the problem of high production cost. Improving the efficiency of separation and collection of the target product is a major challenge to be addressed for production cost reduction.

Non Patent Literature 4 reports that when phaP1, which is a gene that encodes a phasin protein, was disrupted in a bacterium of the genus *Cupriavidus*, the bacterium accumulated a PHA having a larger particle size than that accumulated in the same species of bacterium in which phaP1 was not disrupted. However, the amount of the PHA accumulated in the phaP1-disrupted strain has been found to be significantly small, and thus the phaP1-disrupted strain is not suitable for industrial PHA production.

Non Patent Literature 5 teaches that exposure of microbial bodies accumulating a PHA to stresses such as temperature and pH led to aggregation of the PHA in the cells. However, a microscope image presented in this literature merely shows intracellular adhesion between a very small portion of the PHA particles and fails to demonstrate any change in average particle size of the PHA particles. Further, in this literature, the cells themselves are generally small, and thus the stress exposure is considered to have only a limited effect on the average particle size of the PHA particles.

CITATION LIST

Non Patent Literature

NPL 1: Anderson AJ., et al., *Int. J. Biol. Macromol.*, 12, 102-105 (1990)
NPL 2: Sato S., et al., *J. Biosci. Bioeng.*, 120(3), 246-251 (2015)
NPL 3: Insomphun C., et al., *Metab. Eng.*, 27, 38-45 (2015)
NPL 4: Potter M., et al., *Microbiology*, 151(Pt 3), 825-833 (2005)
NPL 5: Sedlacek P., et al., *Appl. Microbiol. Biotechnol.*, 103(4), 1905-1917 (2019)

SUMMARY OF INVENTION

Technical Problem

A PHA is accumulated in the form of particles in microbial cells. To use the PHA accumulated in the microbial cells as a biodegradable plastic, it is necessary to take the PHA particles out of the cells by disrupting the cells, separate the PHA particles from other cellular components, and collect the PHA particles. Techniques for the separation and collection are broadly classified into a technique using an organic solvent system and a technique using an aqueous system. Since the use of an organic solvent causes high environmental load and involves high cost, the technique using an aqueous system is preferred from the industrial point of view. With the technique using an aqueous system, for example, the PHA particles contained in the cell disruption solution can be separated from the solution by means such as a centrifuge or separation membrane. In this case, the efficiency of the separation and collection depends on the size of the PHA particles. Specifically, a larger size of the PHA particles that has yet to be subjected to the separation step allows the separation and collection to be more easily accomplished by means such as a centrifuge or separation membrane, leading to a lower production cost.

A known approach to size increase of PHA particles is to disrupt microbial cells accumulating PHA particles and then aggregate the PHA particles in the cell disruption solution before separation, thus increasing the size of the particles. However, the degree of aggregation is difficult to control, and impurity removal subsequent to the aggregation is also difficult since the PHA particles trap unwanted substances such as cellular components disrupted into fragments as the particles are aggregating. Thus, the method including aggregating PHA particles in a cell disruption solution is not suitable for industrial PHA production.

In view of the above circumstances, the present invention aims to provide a method of obtaining PHA particles having a large average particle size by aggregating PHA particles in microbial cells.

Solution to Problem

As a result of intensive studies, the present inventors have found that when a PHA-producing microorganism is cultured to obtain microbial bodies accumulating PHA particles and having an average cell size of 2 μm or more and then the microbial bodies are subjected to a heat treatment, PHA particles having an average particle size of 1.8 μm or more can be formed in the microbial bodies. Based on this finding, the inventors have arrived at the present invention.

Specifically, the present invention relates to a method of producing a polyhydroxyalkanoate, the method including the steps of: culturing a polyhydroxyalkanoate-producing microorganism to obtain microbial bodies accumulating polyhydroxyalkanoate particles and having an average cell size of 2 μm or more; and subjecting the microbial bodies to a heat treatment at a temperature higher than a temperature in the culturing to increase an average particle size of the polyhydroxyalkanoate particles in the microbial bodies, wherein the resulting average particle size is equal to or greater than 1.8 μm and equal to or smaller than the average cell size.

Preferably, a ratio of the average particle size of the polyhydroxyalkanoate particles subjected to the heat treatment to the average particle size of the polyhydroxyalkanoate particles not yet subjected to the heat treatment is 1.1 or more.

Preferably, a percentage of a polyhydroxyalkanoate weight to a dry weight of the microbial bodies resulting from the culturing is 80% or more.

Preferably, in a particle size distribution of the polyhydroxyalkanoate particles subjected to the heat treatment, a percentage of polyhydroxyalkanoate particles having a particle size of 1 μm or less is 2.0% by volume or less.

Preferably, the average cell size of the microbial bodies accumulating the polyhydroxyalkanoate particles is 2.2 μm or more.

Preferably, the heat treatment is performed at a temperature of 40 to 100° C. for 5 minutes or more.

Preferably, the heat treatment is performed at a pH of 7.0 or higher.

Preferably, the heat treatment is performed on a culture fluid used in the culturing and containing the microbial bodies.

Preferably, the method further includes the steps of: disrupting the microbial bodies subjected to the heat treatment to obtain a cell disruption solution; and separating the polyhydroxyalkanoate particles from an aqueous phase of the cell disruption solution.

The polyhydroxyalkanoate is preferably a copolymer of two or more hydroxyalkanoates, more preferably a copolymer containing 3-hydroxyhexanoate as a monomer unit, and even more preferably a copolymer of 3-hydroxybutyrate and 3-hydroxyhexanoate.

The polyhydroxyalkanoate-producing microorganism preferably belongs to the genus *Cupriavidus* and is more preferably transformed *Cupriavidus necator*.

Advantageous Effects of Invention

The present invention can provide a method of obtaining PHA particles having a large average particle size by aggregating PHA particles in microbial cells. In the present invention, PHA particles having a large average particle size can be formed in microbial cells before disruption of the microbial bodies, and this can prevent the PHA particles from trapping unwanted substances such as cellular components disrupted into fragments as the particles are aggregating. Additionally, the PHA particles having a large average particle size can be efficiently separated and collected from the cellular components, and this can lead to lowered production cost.

DESCRIPTION OF EMBODIMENTS

Figure 1:
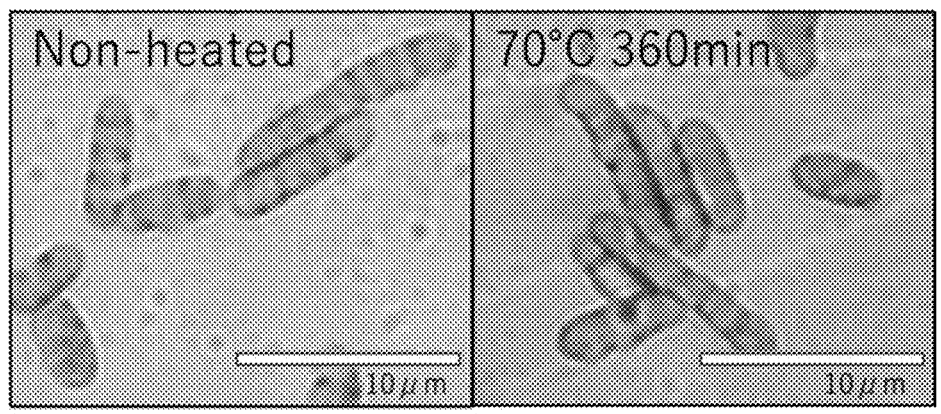
FIG. 1 shows microscope images of cells taken after culture but before heat treatment (left image) and after heat treatment (right image) in Example 1.

Hereinafter, an embodiment of the present invention will be described in detail.

A method of the present embodiment includes the steps of: culturing a PHA-producing microorganism to obtain microbial bodies accumulating PHA particles and having an average cell size of 2 μm or more; and subjecting the microbial bodies to a heat treatment to form PHA particles having an average particle size of 1.8 μm or more in the microbial bodies. The term "average particle size" as used herein exclusively refers to a mean volume diameter.

(PHA-Producing Microorganism)

The PHA-producing microorganism is not limited to a particular type and may be any microorganism that has a PHA-accumulating ability and that can have an average cell size of 2 μm or more after the PHA accumulation. The average cell size of the microorganism need not be invariably 2 μm or more during the culture and is only required to be 2 μm or more after PHA accumulation but before the microorganism is subjected to the heat treatment step. If the average cell size is less than 2 μm after the PHA accumulation, PHA particles having an average particle size of 1.8 μm or more are difficult to form by the heat treatment described later. The average cell size is more preferably 2.2 μm or more, even more preferably 2.4 μm or more, still even more preferably 2.6 μm or more, and particularly preferably 2.8 μm or more. The upper limit of the average cell size is not limited to a particular value. For example, the average cell size may be 10 μm or less or 5 μm or less.

The amount of the PHA accumulated in the PHA-producing microorganism is not limited to a particular range. The percentage of the PHA weight to the dry weight of the microbial bodies, as measured after the PHA accumulation but before the heat treatment step, is preferably 80% or more and more preferably 85% or more. The upper limit of the percentage is not limited to a particular value and may be any value less than 100%. For example, the percentage may be 98% or less or 95% or less.

The PHA-producing microorganism is not limited to a particular type and may be any microorganism that has a PHA synthase gene and accumulates a PHA. Preferred examples of the microorganism include bacteria belonging to the genus *Ralstonia*, the genus *Cupriavidus*, the genus *Wautersia*, the genus *Aeromonas*, the genus *Escherichia*, the genus *Alcaligenes*, and the genus *Pseudomonas*. In view of safety and PHA productivity, bacteria belonging to the genus *Ralstonia*, the genus *Cupriavidus*, the genus *Aeromonas*, and the genus *Wautersia* are more preferred. Even more preferred are bacteria belonging to the genus *Cupriavidus* or the genus *Aeromonas*, and still even more preferred are microorganisms belonging to the genus *Cupriavidus*. Particularly preferred is *Cupriavidus necator*.

The PHA-producing microorganism may be a wild strain having an inherent ability to accumulate a PHA, a mutant strain obtained by artificially mutating the wild strain, or a strain having a PHA accumulating ability attributed to a foreign PHA synthase gene introduced by a genetic engineering technique.

Examples of the PHA-producing microorganism include, but are not limited to, transformed *Cupriavidus necator* such as a minCD-expressed, A2405-disrupted strain and a A1386-deletionally disrupted strain which will be described later.

The PHA produced by the PHA-producing microorganism is not limited to a particular type, and may be any PHA that can be produced by microorganisms. The PHA is preferably any one of the following polymers: a homopolymer of one monomer selected from 3-hydroxyalkanoates having 4 to 16 carbon atoms; a copolymer of one monomer selected from 3-hydroxyalkanoates having 4 to 16 carbon atoms and another hydroxyalkanoate (such as a 2-hydroxyalkanoate, 4-hydroxyalkanoate, 5-hydroxyalkanoate, or 6-hydroxyalkanoate having 4 to 16 carbon atoms); and a copolymer of two or more monomers selected from 3-hydroxyalkanoates having 4 to 16 carbon atoms. Examples of the PHA include, but are not limited to: P(3HB) which is a homopolymer of 3-hydroxybutyrate (abbreviated as 3HB); P(3HB-co-3HV) which is a copolymer of 3HB and 3-hydroxyvalerate (abbreviated as 3HV); P(3HB-co-3HH) (abbreviated as PHBH) which is a copolymer of 3HB and 3-hydroxyhexanoate (abbreviated as 3HH); P(3HB-co-4HB) which is a copolymer of 3HB and 4-hydroxybutyrate (abbreviated as 4HB); and a PHA containing lactic acid (abbreviated as LA) as a constituent component (an example of this PHA is P(LA-co-3HB) which is a copolymer of 3HB and LA). Among these examples, PHBH is preferred in that this polymer has a wide range of applications. The type of the PHA to be produced can be appropriately selected according to the intended purpose and depending on the type of the PHA synthase gene possessed by or introduced into the microorganism used, the type of the metabolic gene involved in synthesis of the PHA, and the culture conditions.

(Culture of PHA-Producing Microorganism)

Culturing the PHA-producing microorganism allows the microbial bodies to accumulate PHA particles therein. The culture of the microorganism can be conducted by a common microbial culture method, and it is sufficient that the microorganism be cultured in a culture medium containing a suitable carbon source. There are no particular limitations on the composition of the culture medium, the method of adding the carbon source, the scale of the culture, the conditions of aeration and stirring, the culture temperature, and the culture time. In terms of accumulation of an adequate amount of PHA, it is preferable to use a method in which the carbon source is added to the culture medium continuously or intermittently.

The carbon source used for the culture may be any carbon source that can be assimilated by the PHA-producing microorganism. Examples of the carbon source include, but are not limited to: sugars such as glucose, fructose, and sucrose; oils such as palm and palm kernel oils (including palm olein, palm double olein, and palm kernel olein which are low-melting fractions obtained through fractionation of palm oil and palm kernel oil), corn oil, coconut oil, olive oil, soybean oil, rapeseed oil, and Jatropha oil; fractions of these oils; by-products formed during refining of these oils; fatty acids such as lauric acid, oleic acid, stearic acid, palmitic acid, and myristic acid; derivatives of these fatty acids; and glycerol. In the case where the PHA-producing microorganism can assimilate gases such as carbon dioxide, carbon monoxide, and methane or alcohols such as methanol and ethanol, any of these gases or alcohols can be used as the carbon source.

In the culture of the PHA-producing microorganism, it is preferable to culture the microorganism using a culture medium containing the carbon source as described above and other nutrient sources including a nitrogen source, an inorganic salt, and another organic nutrient source. Examples of the nitrogen source include, but are not limited to: ammonia; ammonium salts such as ammonium chloride, ammonium sulfate, and ammonium phosphate; peptone; meat extracts; and yeast extracts. Examples of the inorganic salt include potassium dihydrogen phosphate, sodium dihydrogen phosphate, magnesium phosphate, magnesium sulfate, and sodium chloride. Examples of the other organic nutrient source include: amino acids such as glycine, alanine, serine, threonine, and proline; and vitamins such as vitamin B1, vitamin B12, and vitamin C.

(Heat Treatment)

The microbial cells accumulating PHA particles and having an average cell size of 2 µm or more are subjected to a heat treatment at a temperature higher than the temperature at which the microbial cells are cultured. As a result of the heat treatment, the average particle size of the PHA particles can be increased in the microbial cells. The heat treatment is performed before disruption of the microbial cells. The heat treatment may be performed on the culture fluid used in the culture of the PHA-producing microorganism and containing the cultured microbial bodies. Alternatively, the microbial bodies may be collected from the culture fluid and suspended in water or a buffer solution to prepare a suspension, and the heat treatment may be performed on the suspension. Preferably, the heat treatment is performed on the culture fluid used in the culture because in this case the heat treatment is easy.

The heat treatment is not limited to particular conditions and may be performed using any conditions under which the average particle size of the PHA particles can be increased to 1.8 µm or more in the microbial bodies. The conditions are desirably such that the PHA does not leak out of the cells due to destruction of the cytoskeleton. To be specific, the temperature of the heat treatment is a temperature higher than the temperature at which the microbial cells are cultured, and is preferably 40° C. or higher, more preferably 50° C. or higher, even more preferably 60° C. or higher, and still even more preferably 70° C. or higher. The upper limit of the temperature of the heat treatment is not limited to a particular value. For example, the temperature of the heat treatment may be 100° C. or lower and is preferably 90° C. or lower.

The time of the heat treatment is preferably 5 minutes or more, more preferably 30 minutes or more, even more preferably 180 minutes or more, and still even more preferably 360 minutes or more. The upper limit of the temperature of the heat treatment is not limited to a particular value. For example, the time of the heat treatment may be 1 day or less and is preferably 720 minutes or less.

In the heat treatment, the pH of the liquid containing the microbial bodies (e.g., the culture fluid or suspension containing the microbial bodies) is not limited to a particular range and may be lower than 7.0 or may be 7.0 or higher. To further increase the average particle size of the PHA particles by the heat treatment, the pH is preferably 7.0 or higher, more preferably 7.5 or higher, even more preferably 8.0 or higher, and still even more preferably 8.5 or higher. The upper limit of the pH is not limited to a particular value but low enough not to cause disruption of the microbial bodies. For example, the pH may be 12 or lower and is preferably 11 or lower. The pH can be controlled by adding a suitable amount of acid or alkali to the liquid containing the microbial bodies.

The average particle size of the PHA particles in the microbial bodies subjected to the heat treatment is not limited to a particular value, but is equal to or greater than 1.8 µm and equal to or smaller than the average cell size. The average particle size is preferably 1.9 µm or more, more preferably 2.0 µm or more, and even more preferably 2.1 µm or more.

The heat treatment increases the average particle size of the PHA particles in the microbial bodies. To be specific, the ratio of the average particle size of the PHA particles in the microbial bodies subjected to the heat treatment to the average particle size of the PHA particles in the microbial bodies not yet subjected to the heat treatment (average particle size after heat treatment/average particle size before heat treatment) is more than 1.0 and is preferably 1.1 or more, more preferably 1.2 or more, even more preferably 1.3 or more, still even more preferably 1.4 or more, and most preferably 1.5 or more.

The heat treatment causes aggregation of the PHA particles in the microbial bodies, thus reducing the percentage of PHA particles having a small particle size to the total PHA particles. To be specific, in a particle size distribution measured for the PHA particles in the microbial bodies subjected to the heat treatment, the percentage of PHA particles having a particle size of 1 μm or less to the total PHA particles is preferably 2.5% by volume or less, more preferably 2.0% by volume or less, even more preferably 1.5% by volume or less, still even more preferably 1.0% by volume or less, and particularly preferably 0.5% by volume or less.

In the present embodiment, the average cell size of the microbial bodies accumulating PHA particles is as large as 2 μm or more. In such microbial bodies having a large cell size, the percentage of PHA particles having a small particle size tends to be high before the heat treatment. Even in the case where the percentage of PHA particles having a small particle size is high before the heat treatment (e.g., 3.0% by volume or more or 4.0% by volume or more), the heat treatment can reduce the percentage to a value as indicated above. The present embodiment, in which the percentage of PHA particles having a small particle size is reduced, offers the advantage of enabling efficient separation and collection of PHA particles from cellular components.

(Disruption of Cells and Separation and Collection of PHA)

After the microbial bodies accumulating PHA particles are subjected to the heat treatment as described above to increase the average particle size of the PHA particles in the microbial bodies, the microbial bodies are disrupted by a known method to obtain a cell disruption solution. The PHA particles can be separated and collected from an aqueous phase of the cell disruption solution.

The method of disrupting the microbial bodies is not limited to a particular technique, and any known method can be used. For example, a cell disruption solution in which cellular components other than the PHA are dissolved in water can be obtained by disrupting the cells through application of a mechanical shear force or with the aid of a surfactant, an alkali, or an enzyme.

The method of separating and collecting the PHA is not limited to a particular technique, and any known method can be used. For example, the PHA can be collected by separating the PHA particles from the aqueous phase through filtration or centrifugation of the cell disruption solution and then drying the separated particles. The PHA particles produced by the present embodiment and having a large average particle size are preferred because these particles can be efficiently separated and collected using an aqueous system as described above.

EXAMPLES

Hereinafter, the present invention will be described in more detail using examples. The present invention is not limited to the examples. The overall genetic manipulation can be carried out, for example, in a manner as taught in Molecular Cloning (Cold Spring Harbor Laboratory Press (1989)). The enzymes, cloning hosts, and other materials used in the gene manipulation can be purchased from market suppliers and used according to the instructions given by the suppliers. The enzymes are not limited to particular types and may be any enzymes that can be used for gene manipulation.

(Production Example 1) Preparation of MinCD-Expressed, A2405-Disrupted Strain

First, a plasmid for gene deletion was prepared. The preparation was done as follows. PCR using a synthetic oligo DNA was carried out to obtain a DNA fragment (SEQ ID NO: 1) having base sequences upstream and downstream of the A2405 structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB+A2405UD for gene deletion was prepared which had base sequences upstream and downstream of the A2405 structural gene.

Subsequently, an A2405-deletionally disrupted strain was prepared using the plasmid vector pNS2X-sacB+A2405UD for gene deletion. The preparation was done as follows. An *Escherichia coli* 517-1 strain (ATCC 47055) was transformed with the plasmid vector pNS2X-sacB+A2405UD for gene deletion, and the resulting transformed microorganism was co-cultured with a KNK-005 strain on Nutrient Agar (manufactured by Difco Laboratories) to effect conjugal transfer. The KNK-005 strain is a transformed strain produced by introducing an *Aeromonas caviae*-derived PHA synthase gene (a gene that encodes a PHA synthase having the amino acid sequence of SEQ ID NO: 2) onto the chromosome of a *Cupriavidus necator* H16 strain, and can be prepared according to the method described in U.S. Pat. No. 7,384,766.

The cultured microbial bodies obtained as above were inoculated into a Simmons agar medium (2 g/L sodium citrate, 5 g/L sodium chloride, 0.2 g/L magnesium sulfate heptahydrate, 1 g/L ammonium dihydrogen phosphate, 1 g/L potassium dihydrogen phosphate, 15 g/L agar, pH=6.8) containing 250 mg/L kanamycin, and strains grown on the agar medium were selectively collected. Thus, a strain having the plasmid integrated into the chromosome of the KNK-005 strain was obtained. The obtained strain was cultured on Nutrient Broth (manufactured by Difco Laboratories) for two generations, after which the culture broth was diluted and applied onto Nutrient Agar containing 15% sucrose. Strains grown on Nutrient Agar were obtained as strains having lost the plasmid. PCR and analysis using a DNA sequencer were further carried out to isolate one strain from which the start to stop codons of the A2405 structural gene on the chromosome were deleted. This A2405 gene-deleted strain was named "A2405-deletionally disrupted strain".

Next, a plasmid vector pNS2X-sacB-PA-minCD for minCD gene expression was prepared. The preparation was done as follows. PCR using a synthetic oligo DNA was carried out to obtain a DNA fragment (SEQ ID NO: 3) having a promoter sequence, a minCD gene sequence, and a base sequence of an integration site on the genome. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-PA-minCD for minCD gene expression was prepared.

The prepared plasmid vector pNS2X-PA-minCD for minCD gene expression was introduced into the A2405-deletionally disrupted strain by procedures using conjugal transfer as described above. Further, culture and selection on Nutrient Agar containing 15% sucrose were carried out as described above to isolate one strain having a chromosome onto which the promotor sequence and the minCD gene sequence were inserted. The strain thus obtained was named "minCD-expressed, A2405-disrupted strain".

(Production Example 2) Preparation of A1386-Deletionally Disrupted Strain

First, a plasmid for gene deletion was prepared. The preparation was done as follows. PCR using a synthetic oligo DNA was carried out to obtain a DNA fragment (SEQ ID NO: 4) having base sequences upstream and downstream of the A1386 structural gene. The DNA fragment was digested by a restriction enzyme SwaI, and the resulting DNA fragment was joined by a DNA ligase (Ligation High, manufactured by Toyobo Co., Ltd.) to a vector pNS2X-sacB which is described in Japanese Laid-Open Patent Application Publication No. 2007-259708 and which was also digested by SwaI. Thus, a plasmid vector pNS2X-sacB+A1386UD for gene deletion was prepared which had base sequences upstream and downstream of the A1386 structural gene.

Next, the plasmid vector pNS2X-sacB+A1386UD for A1386 gene deletion was introduced into a KNK-005 strain by the vector introduction procedures as described in Production Example 1. Further, one strain from which the start to stop codons of the A1386 structural gene on the chromosome were deleted was isolated by the strain isolation procedures as described in Production Example 1. This A1386 gene-deleted strain was named "A1386-deletionally disrupted strain".

(Comparative Example 1) PHA Production by KNK-005 Strain

A KNK-005 strain was cultured under the conditions described below.
(Culture Media)

The seed culture medium was composed of 1 w/v % Meat-extract, 1 w/v % Bacto-Tryptone, 0.2 w/v % Yeast-extract, 0.9 w/v % $Na_2HPO_4.12H_2O$, and 0.15 w/v % $KH_2PO_4$ (pH=6.8).

The preculture medium was composed of 1.1 w/v % $Na_2HPO_4.12H_2O$, 0.19 w/v % $KH_2PO_4$, 1.29 w/v % $(NH_4)_2SO_4$, 0.1 w/v % $MgSO_4.7H_2O$, 2.5 w/v % palm olein oil, and 0.5 v/v % trace metal salt solution (solution of 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$ in 0.1N hydrochloric acid). Palm olein oil was added as a carbon source in a concentration of 10 g/L at one time.

The PHA production culture medium was composed of 0.385 w/v % $Na_2HPO_4.12H_2O$, 0.067 w/v % $KH_2PO_4$, 0.291 w/v % $(NH_4)_2SO_4$, 0.1 w/v % $MgSO_4.7H_2O$, and 0.5 v/v % trace metal salt solution (solution of 1.6 w/v % $FeCl_3.6H_2O$, 1 w/v % $CaCl_2.2H_2O$, 0.02 w/v % $CoCl_2.6H_2O$, 0.016 w/v % $CuSO_4.5H_2O$, and 0.012 w/v % $NiCl_2.6H_2O$ in 0.1N hydrochloric acid).
(Method of Measuring Percentage of Accumulated PHA to Dried Microbial Bodies)

The percentage of accumulated PHA to dried microbial bodies was measured as follows. The microbial bodies were collected from the culture fluid by centrifugation. The collected microbial bodies were washed with ethanol and freeze-dried to give dried microbial bodies. To 1 g of the dried microbial bodies was added 100 ml of chloroform, and the microbial bodies in chloroform were stirred at room temperature for a day to extract a PHA from the microbial bodies. The residual microbial bodies were removed by filtration, and the filtrate was concentrated using an evaporator to a total volume of 30 ml. To the concentrate was slowly added 90 ml of hexane, and the mixture was left for 1 hour under gentle stirring. The PHA precipitated was collected by filtration and vacuum-dried at 50° C. for 3 hours. The weight of the dried PHA was measured, and the percentage of the accumulated PHA to the dried microbial bodies was calculated.
(Method of Measuring Average Cell Size)

The average cell size was measured as follows. After the culture, the culture fluid was treated at 60° C. for 10 minutes to inactivate the microbial cells. The treated fluid was analyzed with a laser diffraction-scattering particle size distribution analyzer (Microtrac MT3300EXII manufactured by MicrotracBEL Corporation) to measure the mean volume diameter (MV) of the PHA-accumulating cells. The measurement was conducted using standard settings (Permeability: Transparent, Particle refractive index: 1.81, Particle shape: Non-spherical, Solvent refractive index: 1.333).
(Method of Measuring PHA Average Particle Size)

The PHA average particle size was measured as follows. After the culture but before the heat treatment, and after the heat treatment, 0.2 ml of the culture fluid was collected and suspended in 20 ml of a 0.02 w/v % aqueous solution of benzalkonium chloride. To the suspension was added 10 ml of a 10 w/v % aqueous solution of sodium dodecylsulfate, and the resulting mixture was subjected to ultrasonic disruption to give a liquid containing the extracted PHA. The resulting liquid containing the extracted PHA was analyzed with a laser diffraction-scattering particle size distribution analyzer (Microtrac MT3300EXII) to measure the mean volume diameter (MV) of the PHA particles and the percentage (% by volume) of PHA particles having a particle size of 1 μm or less to the total PHA particles. The measurement was conducted using standard settings (Permeability: Transparent, Particle refractive index: 1.81, Particle shape: Non-spherical, Solvent refractive index: 1.333).
(PHA Production Culture)

PHA production culture was performed as follows. First, a glycerol stock (50 μl) of the KNK-005 strain was inoculated into the seed culture medium (10 ml) and cultured for 24 hours to accomplish seed culture. Subsequently, the seed culture fluid was inoculated at a concentration of 1.0 v/v % into a 3 L jar fermenter (MDL-300, manufactured by B.E. Marubishi Co., Ltd.) containing 1.8 L of the preculture medium. The fermenter was operated at a culture temperature of 33° C., a stirring speed of 500 rpm, and an aeration of 1.8 L/min, and the preculture was conducted for 28 hours during which the pH was controlled between 6.7 and 6.8. For the pH control, a 14% aqueous solution of ammonium hydroxide was used.

Next, the preculture fluid was inoculated at a concentration of 5.0 v/v % into a 5 L jar fermenter (MDS-U50, manufactured by B.E. Marubishi Co., Ltd.) containing 2.5 L of the PHA production culture medium. The fermenter was operated at a culture temperature of 33° C., a stirring speed of 420 rpm, and an aeration of 2.1 L/min, and the pH was controlled between 6.7 and 6.8. For the pH control, a 25% aqueous solution of ammonium hydroxide was used. The carbon source was added intermittently. Palm olein oil was used as the carbon source. The culture was continued until the accumulated PHA percentage reached 80% or more. The resulting culture fluid was subjected to a heat treatment, the time and temperature of which were as listed in Table 1-1.

The percentage of accumulated PHA to dried microbial bodies, the average cell size, the PHA average particle sizes before and after heat treatment, and the percentages of 1-μm or smaller PHA particles before and after heat treatment, were measured as described above. Additionally, the rate of heat treatment-induced increase in PHA average particle size (PHA average particle size after heat treatment/PHA average particle size before heat treatment) was calculated. The results are listed in Table 1-1.

The average cell size of the cultured KNK-005 strain was 1.89 μm, the percentage of accumulated PHA to dried microbial bodies was 89%, the PHA average particle size before heat treatment was 1.72 μm, and the percentage of 1-μm or smaller PHA particles before heat treatment was 2.45% by volume. In this comparative example, the average cell size of the cultured PHA-producing microorganism was 1.89 μm and thus, as seen from Table 1-1, the heat treatment gave rise to no increase in the PHA average particle size and little decrease in the percentage of 1-μm or smaller PHA particles.

(Example 1) PHA Production by MinCD-Expressed, A2405-Disrupted Strain

The minCD-expressed, A2405-disrupted strain was cultured under the conditions as described in Comparative Example 1. The resulting culture fluid was subjected to a heat treatment, the time and temperature of which were as listed in Table 1-1. The percentage of accumulated PHA to dried microbial bodies, the average cell size, the PHA average particle sizes before and after heat treatment, the percentages of 1-μm or smaller PHA particles before and after heat treatment, and the rate of heat treatment-induced increase in PHA average particle size are listed in Table 1-1. Additionally, before and after the heat treatment, the cells were placed and dried on a glass slide, then stained with fuchsin, and observed with an optical microscope. The images taken by the microscopic observation are shown in FIG. 1. The cells retained their shape after the heat treatment.

The average cell size of the cultured minCD-expressed, A2405-disrupted strain was 2.95 μm, the percentage of accumulated PHA to dried microbial bodies was 86%, the PHA average particle size before heat treatment was 1.62 μm, and the percentage of 1-μm or smaller PHA particles before heat treatment was 5.08% by volume. In this example, as seen from Table 1-1, the heat treatment increased the PHA average particle size, and the maximum value of the increase rate was 1.72. The percentage of 1-μm or smaller PHA particles was significantly reduced from 5.08% by volume as a result of the heat treatment, and the minimum value of the percentage was 0.00% by volume.

(Example 2) PHA Production by A1386-Deletionally Disrupted Strain

Figure 2:
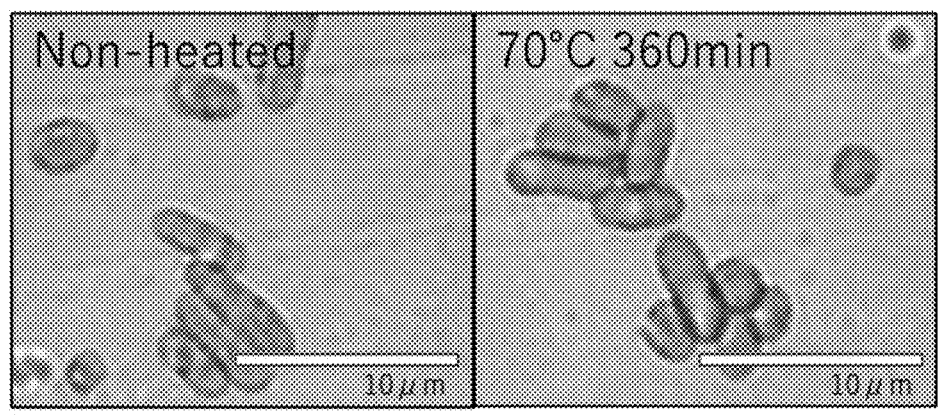
FIG. 2 shows microscope images of cells taken after culture but before heat treatment (left image) and after heat treatment (right image) in Example 2.

The A1386-deletionally disrupted strain was cultured under the conditions as described in Comparative Example 1. The resulting culture fluid was subjected to a heat treatment, the time and temperature of which were as listed in Table 1-2. The percentage of accumulated PHA to dried microbial bodies, the average cell size, the PHA average particle sizes before and after heat treatment, the percentages of 1-μm or smaller PHA particles before and after heat treatment, and the rate of heat treatment-induced increase in PHA average particle size are listed in Table 1-2. Additionally, before and after the heat treatment, the cells were placed and dried on a glass slide, then stained with fuchsin, and observed with an optical microscope. The images taken by the microscopic observation are shown in FIG. 2. The cells retained their shape after the heat treatment.

The average cell size of the cultured A1386-deletionally disrupted strain was 2.48 μm, the percentage of accumulated PHA to dried microbial bodies was 88%, the PHA average particle size before heat treatment was 1.48 μm, the percentage of 1-μm or smaller PHA particles before heat treatment was 10.86% by volume. In this example, as seen from Table 1-2, the heat treatment increased the PHA average particle size, and the maximum value of the increase rate was 1.59. The percentage of 1-μm or smaller PHA particles was significantly reduced from 10.86% by volume as a result of the heat treatment, and the minimum value of the percentage was 0.00% by volume.

The PHA produced in Comparative Example 1 and Examples 1 and 2 was found to be PHBH by HPLC analysis.

TABLE 1-1

| | Average cell size (μm) | PHA average particle size before heat treatment (μm) | Percentage of 1-μm or smaller PHA particles before heat treatment (% by volume) | Heat treatment temperature (° C.) | Heat treatment time (min) | PHA average particle size after heat treatment (μm) | Rate of heat treatment-induced increase in PHA average particle size | Percentage of 1-μm or smaller PHA particles after heat treatment (% by volume) |
|---|---|---|---|---|---|---|---|---|
| Comp. Example 1 | 1.89 | 1.72 | 2.45 | 70 | 30 | 1.73 | 1.01 | 2.26 |
| | | | | | 360 | 1.71 | 0.99 | 2.23 |
| Example 1 | 2.95 | 1.62 | 5.08 | 40 | 5 | 1.84 | 1.14 | 1.73 |
| | | | | | 30 | 1.97 | 1.22 | 1.14 |
| | | | | | 180 | 2.02 | 1.25 | 0.82 |
| | | | | | 360 | 2.08 | 1.28 | 0.92 |
| | | | | 50 | 5 | 2.04 | 1.26 | 0.89 |
| | | | | | 30 | 2.05 | 1.26 | 0.88 |
| | | | | | 180 | 2.04 | 1.26 | 0.79 |
| | | | | | 360 | 2.08 | 1.28 | 0.78 |

TABLE 1-1-continued

| Average cell size (μm) | PHA average particle size before heat treatment (μm) | Percentage of 1-μm or smaller PHA particles before heat treatment (% by volume) | Heat treatment temperature (° C.) | Heat treatment time (min) | PHA average particle size after heat treatment (μm) | Rate of heat treatment-induced increase in PHA average particle size | Percentage of 1-μm or smaller PHA particles after heat treatment (% by volume) |
|---|---|---|---|---|---|---|---|
| | | | 60 | 5 | 2.07 | 1.28 | 0.76 |
| | | | | 30 | 2.13 | 1.31 | 0.53 |
| | | | | 180 | 2.18 | 1.34 | 0.57 |
| | | | | 360 | 2.29 | 1.41 | 0.06 |
| | | | 70 | 5 | 2.18 | 1.35 | 0.76 |
| | | | | 30 | 2.35 | 1.45 | 0.06 |
| | | | | 180 | 2.52 | 1.56 | 0.04 |
| | | | | 360 | 2.61 | 1.61 | 0.02 |
| | | | 80 | 5 | 2.16 | 1.33 | 0.68 |
| | | | | 30 | 2.66 | 1.64 | 0.04 |
| | | | | 180 | 2.72 | 1.68 | 0.02 |
| | | | | 360 | 2.73 | 1.69 | 0.02 |
| | | | 90 | 5 | 2.34 | 1.44 | 0.09 |
| | | | | 30 | 2.78 | 1.72 | 0.02 |
| | | | | 180 | 2.73 | 1.69 | 0.02 |
| | | | | 360 | 2.68 | 1.65 | 0.00 |

TABLE 1-2

| | Average cell size (μm) | PHA average particle size before heat treatment (μm) | Percentage of 1-μm or smaller PHA particles before heat treatment (% by volume) | Heat treatment temperature (° C.) | Heat treatment time (min) | PHA average particle size after heat treatment (μm) | Rate of heat treatment-induced increase in PHA average particle size | Percentage of 1-μm or smaller PHA particles after heat treatment (% by volume) |
|---|---|---|---|---|---|---|---|---|
| Example 2 | 2.48 | 1.48 | 10.86 | 50 | 5 | 1.80 | 1.21 | 2.77 |
| | | | | | 30 | 1.82 | 1.23 | 2.17 |
| | | | | | 180 | 1.90 | 1.28 | 1.08 |
| | | | | | 360 | 2.06 | 1.39 | 0.08 |
| | | | | 60 | 5 | 1.83 | 1.24 | 1.47 |
| | | | | | 30 | 1.88 | 1.27 | 0.86 |
| | | | | | 180 | 2.14 | 1.45 | 0.04 |
| | | | | | 360 | 2.30 | 1.56 | 0.00 |
| | | | | 70 | 5 | 1.95 | 1.32 | 0.67 |
| | | | | | 30 | 2.10 | 1.42 | 0.04 |
| | | | | | 180 | 2.29 | 1.55 | 0.01 |
| | | | | | 360 | 2.31 | 1.56 | 0.02 |
| | | | | 80 | 5 | 1.88 | 1.27 | 1.26 |
| | | | | | 30 | 2.30 | 1.55 | 0.04 |
| | | | | | 180 | 2.30 | 1.55 | 0.02 |
| | | | | | 360 | 2.29 | 1.55 | 0.00 |
| | | | | 90 | 5 | 2.10 | 1.42 | 0.47 |
| | | | | | 30 | 2.35 | 1.59 | 0.02 |
| | | | | | 180 | 2.29 | 1.55 | 0.00 |
| | | | | | 360 | 2.23 | 1.50 | 0.00 |

(Example 3) pH Conditions During Heat Treatment

The A1386-deletionally disrupted strain was cultured in the same manner as in Example 2, and part of the resulting culture fluid was collected. The collected culture fluid was subjected to a heat treatment, during which the pH of the culture fluid was controlled to the values (within +0.1) listed in Table 2. The time and temperature of the heat treatment were as listed in Table 2. For the pH control, a 10% aqueous solution of sodium hydroxide was used. The average cell size, the PHA average particle sizes before and after heat treatment, the percentages of 1-μm or smaller PHA particles before and after heat treatment, and the rate of heat treatment-induced increase in PHA average particle size are listed in Table 2.

The average cell size of the cultured A1386-deletionally disrupted strain was 2.60 μm, the percentage of accumulated PHA to dried microbial bodies was 89%, the PHA average particle size before heat treatment was 1.55 μm, and the percentage of 1-μm or smaller PHA particles before heat treatment was 7.08% by volume. In this example, as seen from Table 2, the heat treatment coupled with control of the pH to 7.0 or higher led to the PHA average particle size being efficiently increased. After the pH control but before the heat treatment, the rate of change in the PHA average particle size was not more than 5%. The heat treatment performed at a pH of 8.5 and a temperature of 70° C. for 30 minutes resulted in an increase rate of 1.58. The percentage of 1-μm or smaller PHA particles was significantly reduced from 7.08% by volume to 0.02% by volume as a result of the heat treatment.

The PHA produced in Example 3 was found to be PHBH by HPLC analysis.

TABLE 2

| | Average cell size (μm) | PHA average particle size before heat treatment (μm) | Percentage of 1-μm or smaller PHA particles before heat treatment (% by volume) | Heat treatment temperature (° C.) | Heat treatment pH | Heat treatment time (min) | PHA average particle size after heat treatment (μm) | Rate of heat treatment-induced increase in PHA average particle size | Percentage of 1-μm or smaller PHA particles after heat treatment (% by volume) |
|---|---|---|---|---|---|---|---|---|---|
| Example 3 | 2.60 | 1.55 | 7.08 | 70 | 6.7 | 30 | 2.03 | 1.31 | 0.49 |
| | | | | | | 120 | 2.05 | 1.32 | 0.04 |
| | | | | | 7.0 | 30 | 2.07 | 1.34 | 0.09 |
| | | | | | | 120 | 2.09 | 1.35 | 0.05 |
| | | | | | 7.5 | 30 | 2.13 | 1.37 | 0.06 |
| | | | | | | 120 | 2.27 | 1.46 | 0.06 |
| | | | | | 8.0 | 30 | 2.21 | 1.43 | 0.04 |
| | | | | | | 120 | 2.42 | 1.56 | 0.08 |
| | | | | | 8.5 | 30 | 2.45 | 1.58 | 0.02 |
| | | | | | | 120 | 2.44 | 1.57 | 0.05 |

The invention claimed is:

1. A method of producing a polyhydroxyalkanoate, the method comprising:
   culturing a polyhydroxyalkanoate-producing microorganism, thereby obtaining microbial bodies having an average cell size of at least 2.4 µm in which polyhydroxyalkanoate particles are accumulated; and
   subjecting the microbial bodies to a heat treatment at a temperature higher than a temperature in the culturing, thereby increasing an average particle size of the polyhydroxyalkanoate particles in the microbial bodies to an average particle size of from 1.8 µm to the average cell size,
   wherein the heat treatment is performed before disruption of the microbial cells, and the heat treatment is performed on a culture fluid used in the culturing and comprising the microbial bodies.

2. The method according to claim 1, wherein a ratio of the average particle size of the polyhydroxyalkanoate particles subjected to the heat treatment to the average particle size of the polyhydroxyalkanoate particles prior to the heat treatment is at least 1.1.

3. The method according to claim 1, wherein a percentage of a weight of the polyhydroxyalkanoate particles to a dry weight of the microbial bodies resulting from the culturing is at least 80%.

4. The method according to claim 1, wherein in the polyhydroxyalkanoate particles subjected to the heat treatment, a percentage of polyhydroxyalkanoate particles having a particle size of 1 µm or less is 2.0% by volume or less.

5. The method according to claim 1, wherein the heat treatment is performed at a temperature of from 40 to 100° C. for at least 5 minutes.

6. The method according to claim 1, wherein the heat treatment is performed at a pH of at least 7.0.

7. The method according to claim 1, further comprising:
   disrupting the microbial bodies subjected to the heat treatment to obtain a cell disruption solution; and
   separating the polyhydroxyalkanoate particles from an aqueous phase of the cell disruption solution.

8. The method according to claim 1, wherein the polyhydroxyalkanoate is a copolymer of at least two hydroxyalkanoates.

9. The method according to claim 8, wherein the polyhydroxyalkanoate is a copolymer containing 3-hydroxyhexanoate as a monomer unit.

10. The method according to claim 9, wherein the polyhydroxyalkanoate is a copolymer of 3-hydroxybutyrate and 3-hydroxyhexanoate.

11. The method according to claim 1, wherein the polyhydroxyalkanoate-producing microorganism belongs to the genus *Cupriavidus*.

12. The method according to claim 1, wherein the polyhydroxyalkanoate-producing microorganism is transformed *Cupriavidus necator*.

13. The method according to claim 1, wherein the heat treatment is performed at a temperature of from 40 to 100° C. for at least 5 minutes and a pH of at least 7.0.

14. The method according to claim 1, wherein the heat treatment is performed at a temperature of from 50 to 90° C. for from 5 to 720 minutes and a pH of from 7.5 to 12.

15. The method according to claim 1, wherein the average cell size of the microbial bodies in which the polyhydroxyalkanoate particles are accumulated is 10 µm or less.

16. The method according to claim 1, wherein the average cell size of the microbial bodies in which the polyhydroxyalkanoate particles are accumulated is 5 µm or less.

17. The method according to claim 1, wherein the heat treatment is performed at a pH of at least 8.0.

18. The method according to claim 1, wherein the heat treatment is performed at a temperature of from 40 to 90° C. for from 5 to 360 minutes.

19. The method according to claim 1, wherein the heat treatment is performed at a pH of from 6.7 to 8.5.

\* \* \* \* \*